United States Patent
Brennan et al.

(10) Patent No.: US 6,403,220 B1
(45) Date of Patent: Jun. 11, 2002

(54) PHOSPHORUS ELEMENT-CONTAINING CROSSLINKING AGENTS AND FLAME RETARDANT PHOSPHORUS ELEMENT-CONTAINING EPOXY RESIN COMPOSITIONS PREPARED THEREWITH

(75) Inventors: David J. Brennan, Midland, MI (US); John P. Everett, Buehl-Neusatz (DE); Bassam S. Nader, Fishers, IN (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/734,904

(22) Filed: Dec. 11, 2000

Related U.S. Application Data
(60) Provisional application No. 60/170,298, filed on Dec. 13, 1999.

(51) Int. Cl.$^7$ ................................................ B32B 27/38
(52) U.S. Cl. ........................... 428/413; 508/14; 508/17; 528/87; 528/88; 528/403; 528/408; 528/419; 528/421; 524/612; 524/414; 524/127; 524/100; 525/525
(58) Field of Search ...................... 568/14, 17; 428/413; 528/87, 88, 403, 408, 419, 421; 524/612, 414, 127, 100; 525/525

(56) References Cited

U.S. PATENT DOCUMENTS

| | | | |
|---|---|---|---|
| 4,066,628 A | 1/1978 | Ashida et al. | 260/77.5 |
| 4,765,898 A | * 8/1988 | Buys et al. | |
| 4,925,901 A | 5/1990 | Bertram et al. | 525/482 |
| 4,973,631 A | 11/1990 | McGrath et al. | 525/534 |
| 5,036,135 A | 7/1991 | von Gentzkow et al. | 524/786 |
| 5,066,735 A | 11/1991 | Walker et al. | 525/482 |
| 5,086,156 A | 2/1992 | McGrath et al. | 528/108 |
| 5,112,931 A | 5/1992 | Potter et al. | 528/45 |
| 5,364,893 A | 11/1994 | von Gentzkow et al. | 523/429 |
| 5,376,453 A | 12/1994 | von Gentzkow et al. | 428/415 |
| 5,587,243 A | 12/1996 | von Gentzkow et al. | 428/413 |
| 5,759,690 A | 6/1998 | von Gentzkow et al. | 428/413 |
| 5,817,736 A | 10/1998 | von Gentzkow et al. | 528/108 |

FOREIGN PATENT DOCUMENTS

| | | |
|---|---|---|
| EP | 0 458 502 A2 | 11/1991 |
| EP | 0 526 488 B1 | 11/1994 |
| EP | 0 825 217 A1 | 2/1998 |
| WO | WO 96/12751 | 5/1996 |
| WO | WO 98/07731 | 2/1998 |
| WO | WO 99/00451 | 1/1999 |

OTHER PUBLICATIONS

Cho, et al. "Novel flame retardant epoxy resins," Polymer Bulletin, vol. 41, pp. 45–52 (1998).
Derwent Abstract of DE 4308184.
Derwent Abstract of DE 4308185.
Derwent Abstract of EP 0 754 728.
Derwent Abstract of EP 0 806 429.
Derwent Abstract of JP 61,134,395.
Dhawan, et al. "Metallation induced rearrangement of tri-arylphosphates to tris (2–hydroxyaryl) phospine oxides," Synthetic Communications, vol. 17(4), pp. 465–468 (1987).
"Encyclopedia of Polymer Science and Engineering," "Epoxy Resins," vol. 6, pp. 348–356 (1986).
"Epoxy Resins Chemistry and Technology," C. A. May, pp. 506–512 (1988).
"Handbook of Epoxy Resins," H. E. Lee and K. Neville, section 11–14 (1967).

* cited by examiner

*Primary Examiner*—Robert Dawson
*Assistant Examiner*—Kuo-Liang Peng

(57) ABSTRACT

Novel phosphorus element-containing crosslinking agents for epoxy resin compositions based on an isomeric mixture of tris(2-hydroxyphenyl)-phosphine oxide compounds. Epoxy resins cured or crosslinked with the crosslinking agents of this invention yield non-halogenated, ignition resistant epoxy resin formulations. The ignition resistant epoxy resin formulations are advantageously used for making laminates for printed wiring boards and composite materials.

56 Claims, No Drawings

PHOSPHORUS ELEMENT-CONTAINING CROSSLINKING AGENTS AND FLAME RETARDANT PHOSPHORUS ELEMENT-CONTAINING EPOXY RESIN COMPOSITIONS PREPARED THEREWITH

This application claims the benefit of U.S. Provisional Application No. 60/170,298, filed Dec. 13, 1999.

BACKGROUND OF THE INVENTION

This invention relates to new crosslinking agents for epoxy resin compositions, more particularly to phosphorus element-containing compounds useful as crosslinking agents for epoxy resin compositions to yield non-halogenated, ignition resistant phosphorus element-containing epoxy resin formulations. Even more particularly, the new phosphorus element-containing crosslinking agents of the present invention are based on isomeric mixtures of tris(2-hydroxyphenyl)phosphine oxides having the following general chemical structure of Formula I:

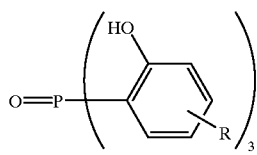

Formula I wherein R may be independently a hydrogen or a $C_1$–$C_{10}$ alkyl group such as methyl, ethyl, propyl, butyl, etc. The flame retardant epoxy resin formulations of this invention are advantageously used for making laminates for printed wiring boards and composite materials.

It is known to make electrical laminates and other composites from a fibrous reinforcement and an epoxy-containing matrix resin. Examples of suitable, processes usually contain the following steps:

(1) an epoxy-containing formulation is applied to or impregnated into a substrate by rolling, dipping, spraying, other known techniques and/or combinations thereof. The substrate is typically a woven or non-woven fiber mat containing, for instance, glass fibers or paper.

(2) The impregnated substrate is "B-staged" by heating at a temperature sufficient to draw off solvent in the epoxy formulation and optionally to partially cure the epoxy formulation, so that the impregnated substrate can be handled easily. The "B-staging" step is usually carried out at a temperature of from 90° C. to 210° C. and for a time of from 1 minute to 15 minutes. The impregnated substrate that results from B-staging is called a "prepreg". The temperature is most commonly 100° C. for composites and 130° C. to 200° C. for electrical laminates.

(3) One or more sheets of prepreg are stacked or laid up in alternating layers with one or more sheets of a conductive material, such as copper foil, if an electrical laminate is desired.

(4) The laid-up sheets are pressed at high temperature and pressure for a time sufficient to cure the resin and form a laminate. The temperature of this lamination step is usually between 100° C. and 230° C., and is most often between 165° C. and 190° C. The lamination step may also be carried out in two or more stages, such as a first stage between 100° C. and 150° C. and a second stage at between 165° C. and 190° C. The pressure is usually between 50 N/cm² and 500 N/cm². The lamination step is usually carried out for a time of from 1 to 200 minutes, and most often for 45 to 90 minutes. The lamination step may optionally be carried out at higher temperatures for shorter times (such as in continuous lamination processes) or for longer times at lower temperatures (such as in low energy press processes).

(5) Optionally, the resulting laminate, for example a copper-clad laminate, may be post-treated by heating for a time at high temperature and ambient pressure. The temperature of post-treatment is usually between 120° C. and 250° C. The post-treatment time usually is between 30 minutes and 12 hours.

It is conventional in the preparation of epoxy-containing laminates to incorporate into the epoxy resin composition various additives to improve the flame-retardancy of the resulting laminate. Many types of flame retardant additives have been suggested, but the additives which are most widely used commercially are halogen-containing additives, such as tetrabromo-diphenylolpropane, or epoxy resins prepared by reacting diglycidyl ether of bisphenol-A with tetrabromodiphenylolpropane. Typically, in order to reach the desired fire retardancy level (V-0 in the standard "Underwriters Laboratory" test method UL 94), levels of such bromine-containing flame retardant additives are required which provide a bromine content of from 10 wt % to 25 wt % based on the total polymer weight in the product.

Although halogen-containing fire-retardant additives such as tetrabromodiphenylolpropane are effective, they are considered by some to be undesirable from an environmental standpoint, and in recent years there has been increasing interest in the formulation of halogen-free epoxy resins, which are able to meet the fire retardancy requirements.

Proposals have been made to use phosphorus-based flame retardants instead of halogenated fire retardants in epoxy resin formulations as described in, for example, EP A 0384939, EP A 0384940, EP A 0408990, DE A 4308184, DE A 4308185, DE A 4308187, WO A 96/07685, and WO A 96/07686. In these formulations a phosphorus flame retardant is pre-reacted with an epoxy resin to form a di- or multifunctional epoxy resin which is then cured with an amino cross-linker such as dicyandiamide, sulfanilamide, or some other nitrogen element-containing cross-linker to form the network.

There are some commercially available phosphorus-based fire retardant additives which may be useful for replacing halogen-containing fire-retardant additives. For example, Amgard™ V19 and Antiblaze™ 1045 (previously Amgard™ P45) supplied by Albright and Wilson Ltd, United Kingdom, are commercially available phosphonic acid ester fire retardant materials. These phosphonic acid esters, may be solids or liquids.

Alkyl and aryl substituted phosphonic acid esters are compatible with epoxy resins. In particular lower (i.e., $C_1$–$C_4$) alkyl esters of phosphonic acid are of value because they contain a high proportion of phosphorus, and are thus able to impart good fire retardant properties upon resins in which they are incorporated. However, the phosphonic acid esters are not satisfactory as a substitute for halogenated flame retardants in epoxy resins for the production of electrical laminates, because the use of phosphonic acid esters in amounts sufficient to provide the necessary flame retardancy increases the tendency of the resulting cured epoxy resin to absorb moisture. The moisture absorbency of the cured laminate board is very significant, because laminates containing high levels of moisture tend to blister and fail, when introduced to a bath of liquid solder at temperatures around 260° C., a typical step in the manufacture of printed wiring boards.

Another system, which utilizes a phosphorus-based flame retardant, is described in EP A 0754728. EP A 0754728 describes the production of a flame retardant epoxy resin system by blending an epoxy resin with a cyclic phosphonate as a flame retardant and incorporating the cyclic phosphonate into the cured resin. The epoxide resin and phosphonate mixture is crosslinked with a polyamine such as triethylamine, tetra amine, polyamido amines, multi basic acids or their anhydrides for example phthalic anhydride or hexahydrophthalic anhydride. EP A 0,754,728 indicates that large quantities, such as in excess of 18 wt %, of the phosphorus additive are needed in order for the resin system to meet UL 94 V-0.

WO 99/00451 discloses flame retardant epoxy resin compositions utilizing phosphonic acid esters. WO 99/00451 discloses the reaction of a phosphonic acid ester with an epoxy resin in the presence of a catalyst and a nitrogen-containing crosslinking agent. The crosslinking agent has an amine functionality of at least 2 and is preferably dicyandiamide. The epoxy resins described in WO 99/00451 have improved flame retardant properties at low levels of phosphonic acid ester flame retardant. However, there is still a need in the industry for a flame retardant epoxy resin with improved Tg and flame retardant properties.

As aforementioned, halogen-containing phenol compounds such as tetrabromobisphenol-A (TBBA) are well known materials used in epoxy resins, specifically for use in the manufacture of FR-4 laminates for printed circuit boards. Halogen-containing compounds, specifically bromine-containing materials have the disadvantages of corrosive acidic components, e.g. HBr, released at high temperatures. It would be desirous to provide a non-halogenated material as a fire retardant additive to replace halogen-containing phenol compounds such as TBBA.

The prior art describes the use of certain phosphorus element-containing compounds as crosslinking or curing agents for use with epoxy resins as a way to introduce a phosphorus element into epoxy resin systems. For example, U.S. Pat. Nos. 4,973,631 and 5,086,156 describe the use of difunctional phosphine oxide crosslinkers such as a triphenyl phosphine oxide epoxy curing agent and a trihydrocarbyl phosphine oxide epoxy curing agent having the following chemical structural formula:

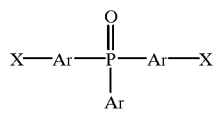

wherein Ar is an phenyl ring and the X moieties have an active hydrogen and include an amine, hydroxy, carboxy, anhydride and thiol moieties.

JP 61,134,395 [86,134,395] teaches the use of tris(3-hydroxyphenyl)phosphine oxide having the following chemical structural formula:

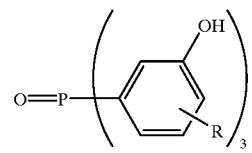

as a crosslinking agent for epoxy resins.

The above-mentioned prior art compositions are not easily prepared and require exotic preparation procedures. It would be advantageous to provide a compound that can be derived from practical, industrial scale raw materials; and thus, would offer an economic advantage over the prior art processes.

The prior art describes the use of phosphates [OP(OR)$_3$] and other compounds with P—O—C units in epoxy resin formulations. Such resins do not provide a satisfactory resistance to water uptake. It would be desirous to provide compounds such as triarylphosphine oxides which do not contain P—O—C bonds, and therefore, do not suffer the disadvantages of the prior art compounds having P—C units. It would be desirous to provide phosphorus compounds with P—C linkages having superior resistance to water uptake when compared to phosphorus compounds with P—O—C units.

Phosphorus-containing compounds have been used heretofore in a variety of epoxy-based polymer systems including for example FR-4 laminates for printed circuit boards, container coatings, as well as high-molecular weight epoxy-based thermoplastics. A driving force for this work has been the search for non-halogenated alternatives to brominated epoxy resins. For a variety of reasons, brominated flame retardants have been deemed environmentally unsound and the use of brominated flame retardants in flame retardant epoxy resins applications has been continually threatened by legislation. Thus, there is a need to address this issue.

Commercially available non-brominated flame retardants have been used as replacements for tetrabromobisphenol-A (TBBA) in FR-4 laminates for printed circuit boards. Although most of these materials are found to meet the requirements for ignition and heat resistance, excessive moisture uptake in the board is found to be the main problem with their use. The presence of excess moisture cause the laminate boards to fail blister resistance testing. Phosphorus-containing species (phosphates, phosphonates, and phosphoramides) that contained P—O and P—N bonds, are believed to be the cause of excessive moisture uptake due to their polarity. Thus, it is desired to provide materials that contain P—C bonds instead of P—O or P—N bonds in FR-4 laminate applications. It would be advantageous if such materials would reduce the amount of water absorbed by the finished laminate board. It is desired to provide compounds, which improve resistance to moisture uptake in the laminate boards, while maintaining the requirements of excellent Tg and ignition resistance.

SUMMARY OF THE INVENTION

The present invention is directed to epoxy resins which meet the desirable standards of fire retardancy without the need for halogen-containing flame retardants, or at least employing significantly lower levels of such halogen-containing flame retardants than is conventional in the art.

One aspect of the present invention is directed to new phosphorus element-containing crosslinking agents for epoxy resin compositions, more particularly crosslinking agents based on an isomeric mixture of two or more isomers of tris(2-hydroxyphenyl)phosphine oxides having the general chemical structure of Formula I as follows:

Formula I

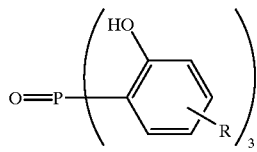

wherein R is independently a hydrogen or a $C_1$–$C_{10}$ alkyl group such as methyl, ethyl, propyl, butyl, etc.

Another aspect of the present invention is directed to curable epoxy resin compositions containing a curable epoxy resin and, as a phosphorus element-containing crosslinking agent, an effective curing amount of a tris(2-hydroxyphenyl)phosphine oxide having the general chemical structure of Formula I as follows:

Formula I

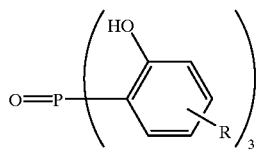

wherein R is independently a hydrogen or a $C_1$–$C_{10}$ alkyl group such as methyl, ethyl, propyl, butyl, etc.

Yet another aspect of the present invention is directed to preparing a non-halogenated, ignition resistant epoxy resin formulation useful for making laminates for printed wiring boards and composite materials using the above phosphorus element-containing crosslinking agent of Formula I.

Hydroxyphenylphosphine oxides, such as those having the above general Formula I, which contain less hydrophilic phosphorus-phenyl units, are advantageously used for the synthesis of epoxy-based thermosets. Compounds of Formula I can be incorporated into epoxy-based polymers via covalent linkages. Improvements in glass transition temperatures and ignition resistance are realized when the resultant phosphorus-containing polymers are compared to conventional bisphenol-A based epoxy thermoplastics. The phenol-functionalized phosphine oxide species of the present invention may be useful as replacements for tetrabromobisphenol-A in FR-4 laminates applications.

It is an objective of the present invention to provide a cross-linking agent which yields superior performance when compared to the previously known commercially available non-halogenated materials.

Still another aspect of the present invention is directed to a compound which includes the glycidyl ether derivatives of Formula I, shown as the following chemical structural Formula V:

Formula V

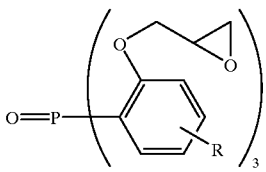

wherein R is as defined above.

Yet another aspect of the present invention is directed to epoxy vinyl ester resins produced by reacting the compound of Formula V above with carboxylic acids which contain an unsaturated functionality to produce the compounds as shown in the following chemical structure of Formula VIII:

Formula VIII

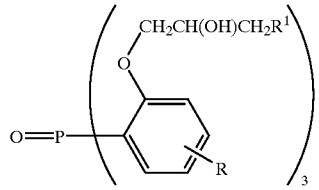

wherein R is defined above and $R^1$ is a moiety containing an unsaturated functionality such as a moiety having the following formula:

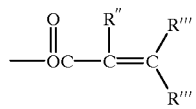

where R" is a hydrogen or an alkyl group from $C_1$–$C_{20}$ and R''' may be a hydrogen, an alkyl group from $C_1$–$C_{20}$, or a carboxylic acid group or ester derivatives thereof. For example R' may be a methacrylate, acrylate, maleate, fumarate and the like.

DETAILED DESCRIPTION OF THE PREFERRED EMBODIMENTS

In its broadest scope, the present invention is directed to a new phosphorus element-containing crosslinking agent advantageously used in epoxy-based formulations for preparing a flame retardant epoxy resin composition substantially free of halogen. The cross linkers of the present invention are preferably used as curing agents for epoxy formulations used in FR-4 laminates for printed circuit boards. Generally, the flame retardant composition includes (I) a non-halogenated epoxy resin material and (II) a phosphorus element-containing crosslinking agent.

A resin which is "substantially free of halogen" means that the resin is completely free of halogen, i.e. 0% halogen, or that the resin contains some minor amount of halogen that does not affect the properties or performance of the resin, and is not detrimental to the resin. Usually resins which have not been halogenated with a halogen-containing compound are "substantially free of halogen".

"Substantially free of halogen", therefore, herein generally means that the resin contains less than 10 weight percent, preferably less than about 5 weight percent, more preferably less than about 1 weight percent, even more preferably less than 0.5 weight percent and most preferably zero weight percent of a halogen in the resin composition.

In order to obtain satisfactory ignition resistance, i.e. flame retardancy, and still obtain the benefit of resistance to water absorption, it is important that the amount of the phosphorus element in the epoxy resin composition is from about 0.2 wt % to about 5 wt %, preferably from about 0.5 wt % to about 3.5 wt %, even more preferably from about 1 wt % to about 3 wt %, and most preferably from about 1.5 wt % to about 2.8 wt %, based on the total of the solid resin composition.

The phosphorus element-containing crosslinking agent (II) of the present invention is preferably one or more compounds, or an isomeric mixture of two or more isomer compounds, having the following general chemical structural Formula I:

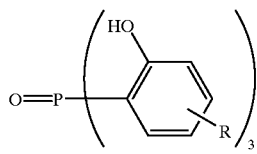

Formula I wherein R is independently a hydrogen or a $C_1$–$C_{10}$ alkyl group including for example, methyl, ethyl, propyl, butyl, etc.

Specific examples of the crosslinkers (II) of the present invention may include those having the following chemical structural Formulas II–IV:

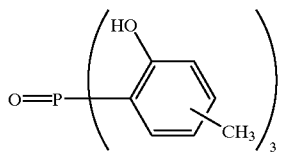

Formula II

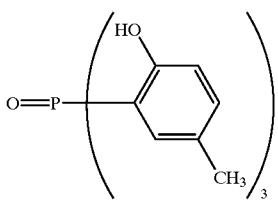

Formula III

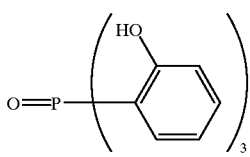

Formula IV

The compounds of Formulas III and IV above are specific compounds wherein a $CH_3$ group is in the 5 position of the phenyl ring as shown in Formula III or wherein a hydrogen is in the 3, 4, 5, and 6 positions of the phenyl ring as shown in Formula IV; and such compounds are described in Synthetic Communications, 1987, 17(4), 465–468. Heretofore, the compounds of Formulas III and IV have not been used as crosslinkers for epoxy resins, particularly for making flame retardant compositions.

The crosslinkers of the above Formula II are preferably used in the present invention. Formula II represents an isomeric mixture of two or more different triaryl phosphine oxide isomer compounds wherein the R group is a methyl and the methyl can be in the 3, 4, 5 or 6 position in each of the phenyl rings. The isomeric mixture of Formula II is new. A more preferred embodiment of the isomeric mixture of Formula II used in the present invention is when the mixture contains at least one of the isomers having at least one 2-hydroxy-4-methyl phenyl moiety and/or at least one of the isomers having at least one 2-hydroxy-5-methylphenyl moiety.

The ratio of 2-hydroxy-4-methylphenyl moiety to the 2-hydroxy-5-methyl phenyl moiety is generally dependent on the moiety ratios of the starting precursor; and the ratio can range from 99:1 to 1:99 and preferably, the ratio is from about 70:30 to about 30:70.

The cross-linker (II) of the present invention is preferably used in the epoxy resin composition in an amount of from about 50% to about 150% of the stoichiometric amount needed to cure the epoxy resin and more preferably from about 75% to about 125% of the stoichiometric amount needed to cure the epoxy resin, even more preferably from about 85% to about 110% of the stoichiometric amount needed to cure the epoxy resin.

Formulations that use the crosslinking agent of Formula II yield laminates with excellent glass transition temperatures (Tg) of from about 50° C. to about 180° C. and an ignition resistance of V-0/V-1.

Formulations made using the crosslinker of Formula II yield laminates have a Tg of preferably greater than 120° C., more preferably greater than 135° C., and most preferably greater than 150° C. The crosslinker of Formula II also provides good resistance to water uptake for a phosphorus-containing additive/comonomer, with a moisture pickup of preferably less than about 1%, more preferably less than about 0.5%, and most preferably less than about 0.3% after about 40 minutes exposure time in a steam autoclave (known in the industry as the "pressure cooker test"). Thus, compounds of the general chemical structural Formula I, specifically the compound of Formula II, are superior to other known phosphorus-containing compounds used to prepare non-halogenated FR-4 laminates for printed circuit boards.

The compounds of Formulas I–IV may be prepared by a method described in Synthetic Communications, 1987, 17(4), pp. 465–468, incorporated herein by reference. Generally, the method of preparation of the compounds of the present invention involves the reaction of a corresponding precursor such as a triarylphosphate, with lithium diisopropyl amide in tetrahydrofuran (THF) solvent at −78° C. For example, commercially available triarylphosphate precursors such as tris(p,m-cresyl)phosphate and triphenylphosphate can be used as starting materials to prepare, on an industrial scale, the compounds of Formula II and Formula IV, respectively.

The crosslinker of Formula II is preferably soluble in aprotic and/or protic solvents commonly used for making epoxy resin formulations, particularly for use in laminate applications. The solvents include for example acetone, methylethyl ketone, methanol, ethanol, Dowanol PM*, N-methylpyrrolidone, dimethylforamide and the like. The solubility of the crosslinker is preferably greater than 30% solids content, more preferably greater than 40% solids contents and most preferably greater than 50% solids contents. The compounds of Formulas III and IV are high melting crystalline solids which are useful as crosslinking agents in other applications such as coatings, adhesives and composites.

An additional embodiment of the present invention is a compound which includes the glycidyl ether derivatives of Formula I, shown as the following chemical structural Formula V:

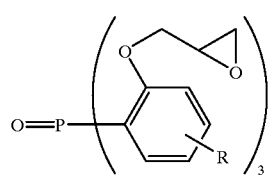

Formula V wherein R is as defined above.

The compounds of Formula V can be produced by epoxidizing the compounds of Formula I using well known techniques in the art such as reacting the compounds of Formula I with an epihalohydrin such as epichlorohydrin to prepare the epoxy resin.

The resulting epoxy resin of Formula V can be advantageously used per se as an epoxy resin base material, such as those described herein as the non-halogenated epoxy resin materials of component (I), for making a flame retardant composition which is curable with any curing agent. More particularly, the curing agent used can also be the phosphorus element-containing crosslinking agent (II) disclosed herein as Formula I. In another embodiment, the compound of Formula V may also be used in combination with other phosphorus element-containing compounds. The combination of the compounds of Formula V and Formula I produce curable compositions which can be used in applications such as flame retardant coatings, laminates, composites and adhesives.

More beneficially, the compounds of Formula V can be used in laminate applications to produce laminates which have a reduced water up-take because of the P—C bonds as opposed to those compounds having a P—O—C bonds.

In still another embodiment of the present invention, the previously described epoxy resin compound of Formula V can be further reacted with a carboxylic acid material which contains an unsaturated functionality to make a vinyl ester resin as shown in the following chemical structure of Formula VIII:

Formula VIII

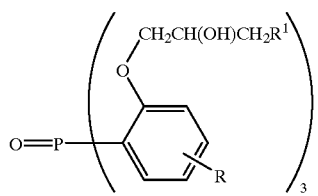

wherein R is defined above and $R^1$ is a moiety containing an unsaturated functionality such as a moiety having the following formula:

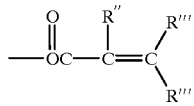

where R" is a hydrogen or an alkyl group from $C_1$–$C_{20}$ and R'" may be a hydrogen, an alkyl group from $C_1$–$C_{20}$, or a carboxylic acid group or ester derivatives thereof. For example $R^1$ may be a methacrylate, acrylate, maleate, fumarate and the like.

Preferably, the epoxy vinyl ester resins of Formula VIII is produced by reacting a carboxylic acid material having an unsaturated functionality such as acrylic acid, methacrylic acid, maleic acid, fumaric acid, and the like.

The amount of carboxylic acid material used is sufficient to completely react the acid functionality with all of the epoxy groups, i.e., stoichiometric amounts using techniques well known in the art. The epoxy vinyl ester resins may also be used with commonly reactive diluents such as styrene, divinyl benzene, and p-methyl styrene and other reactive diluents known in the art. The diluents are used for ease of fabricating, for example, composites; and for improving the properties of the final composites produced.

The compounds of Formula VIII are advantageously used to produce compositions which can be used in applications such as flame retardant coatings, laminates, composites and adhesives.

The crosslinking agent (also referred to as a "hardener" or "curing agent" herein) of the present invention may be used alone, or in combination with one or more second different crosslinking agents, i.e., a co-crosslinking agent (VII). For example, the co-crosslinking agent used in the present invention may be selected from a multifunctional phenolic crosslinker, a nitrogen-containing crosslinker, styrenic maleic anhydride (SMA) or other phosphorus element-containing compounds.

In one optional embodiment, the composition of the present invention may include, as an additional crosslinking agent or co-crosslinker (VII), a multi-functional phenolic cross-linker which contains at least two or more functionalities. Examples of such phenolic crosslinking agents are described in co-pending U.S. Patent Application entitled "Flame Retardant Phosphorus Element-Containing Epoxy Resin Compositions" Ser. No. 09/734,537, filed of even date herewith, and incorporated by reference. For example, the multi-functional phenolic cross-links are preferably novolacs or cresol novolacs obtained by the condensation of phenols, cresols, xylenols or other alkyl phenols with formaldehyde. In the present invention, the resoles may also be used as the multi-functional phenolic crosslinker.

Preferably, if a multi-functional phenolic cross-linker is used in the present invention, the cross-linker has the following chemical structural Formula VI:.

Formula VI

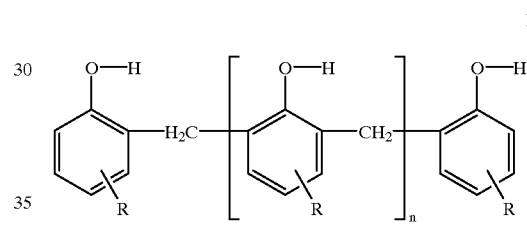

wherein "R" is hydrogen or a $C_1$–$C_3$ alkyl, e.g., methyl and "n" is 0 or an integer from 1 to 10. "n" preferably has an average value of from 0 to 5.

In another embodiment, the composition of the present invention may include as an additional crosslinking agent, a nitrogen-containing cross-linker (VII), used as a subsidiary cross-linker in addition to the phosphorus element-containing cross-linker (II), and with or without the multi-functional phenolic cross-linker. The nitrogen-containing co-crosslinking crosslinking agent preferably has an amine functionality of at least 2. Suitable multi-functional cross-linkers are described in numerous references such as Vol. 6 Encyclopedia of Poly. Sci. & Eng., "Epoxy resins" at 348–56 (J. Wiley & Sons 1986). Examples of suitable nitrogen-containing co-crosslinkers useful in the present invention may be found in WO 99/00451, incorporated herein by reference; and include for example, include polyamines, polyamides, sulpfhanilamide, diaminodiphenylsulfone and diaminodiphenyl methane and dicyandiamide, substituted dicyandiamide, 2,4-diamino-6-phenyl- 1,3,5-triazin. When a nitrogen-containing crosslinker is used in the present formulation, the preferred nitrogen-containing co-crosslinkers are dicyandiamide, sulfainilamide and, 2, 4-diamino-6-phenyl-1, 3, 5-triazine, more preferable sulfanilamide issued.

Another preferred embodiment of co-crosslinkers (VII) useful in the present invention are described in U.S. Pat. Application Serial No. 09/008983, entitled Latent Catalysts for Epoxy Curing Systems, filed Jan. 20, 1998, by Gan et al; incorporated herein by reference; and which include, for example, copolymers of styrene and maleic anhydride having a molecular weight ($M_w$) in the range of from 1500 to 50,000 and an anhydride content of more than 15 percent. Commercial examples of these materials include SMA 1000, SMA 2000, and SMA 3000 having styrene-maleic anhydride ratios of 1:1, 2:1, and 3:1 respectively and having molecular weights ranging from 6,000 to 15,000; and which are available from Elf Atochem S.A.

When one or more co-crosslinkers are used in the present invention, the co-crosslikers are present in an amount to cross-link less than 40% of stoichiometric amount needed to cure the epoxy resin. Preferably, the amount of the co-crosslinking agent in the epoxy resin is from 0 to 40% of the stoichiometric quantity needed to cure the epoxy content of the epoxy resin in the formulation.

The non-halogenated epoxy resin material (I) of the present invention may be selected from: (A) a non-halogenated epoxy resin; (B) a non-halogenated, phosphorus element-containing epoxy resin; (C) a mixture of:(1) a non-halogenated, non-phosphorus element-containing epoxy resin, and (2) a phosphorus element-containing compound; (D) the reaction product of: (1) a non-halogenated epoxy resin; and (2) a phosphorus element-containing compound; or (E) a combination of two or more of components (A) to (D).

Generally, the non-halogenated epoxy resin material (I) used in the present invention is a material which possesses on average more than 1 and preferably at least 1.8, more preferably at least 2 epoxy groups per molecule. In the broadest aspect of the present invention, the epoxy resin material may be any saturated or unsaturated aliphatic, cycloaliphatic, aromatic or heterocyclic compound which possesses more than one 1,2-epoxy group.

The non-halogenated epoxy resins (A) useful in the present invention include polyepoxides. The polyepoxide compound useful in the present invention is suitably a compound which possesses an average of from 1.9 to 2.1 1,2-epoxy groups per molecule. In general, the polyepoxide compound is saturated or unsaturated aliphatic, cycloaliphatic, aromatic or heterocyclic compound which possesses more than one 1,2-epoxy group. The polyepoxide compound can be substituted with one or more substituents which are non reactive with the isocyanate groups such as lower alkyls and halogens. Such polyepoxide compounds are well known in the art.

Illustrative polyepoxide compounds useful in the practice of the present invention are described in the *Handbook of Epoxy Resins* by H. E. Lee and K. Neville published in 1967 by McGraw Hill, New York and U.S. Pat. No. 4,066,628. Examples of suitable aromatic polyepoxides are bisphenol-A, bisphenol-F, bisphenol-AD, bisphenol-S, tetramethyl bisphenol-A, tetramethyl bisphenol-F, tetramethyl bisphenol-AD, tetramethyl bisphenol-S, tetrabromobisphenol-A, tetrachlorobisphenol-A, biphenols such as 4,4'-biphenol or 3,3',5,5'-tetramethyl-4,4'-biphenol, and dihydroxynaphthalene. Examples of suitable aliphatic polyepoxides are diglycidyl esters of hexahydrophthalic acid and diglycidyl esters of dicarboxylic acids, epoxidized polybutadiene, epoxidized soyabean oil, and epoxidized diols. Cycloaliphatic epoxides include, for example, 3,4-epoxy-6-methylcyclohexyl carboxylate and 3,4-epoxycyclohexyl carboxylate. Examples of heterocyclic epoxy compounds are diglycidylhydantoin or triglycidyl isocyanurate (TGIC).

Preferred polyepoxides are glycidyl compounds of bisphenol-A, of bisphenol-F, of tetrabromobisphenol-A and of 3,3',5,5'-tetramethyl-4,4-biphenol. Mixtures of any two or more polyepoxides can also be used in the practice of the present invention Examples of a non-halogenated, phosphorus element-containing epoxy resin (B) useful in the composition of the present invention include:

1. Bisglycidylphenylphosphate as illustrated by the following chemical formula:

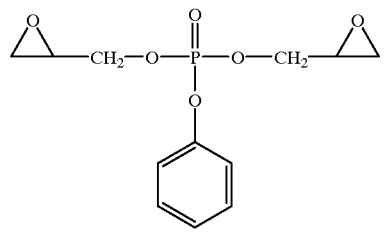

2. The epoxy phosphine oxides described in S. V. Levchik, G. F. Levchik, A. V. Antonov, M. Yu. Yablokova, O. I. Tuzhikov, O. O. Tuzhikov and L. Costa, 1999 including for example the following compounds:

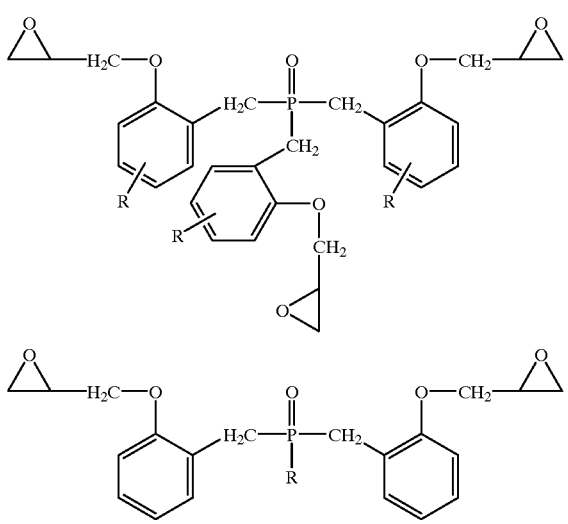

wherein R is as previously defined; and

3. Aryl phosphinate epoxy ether 10-(2',5'-bis (glycidyloxy)phenyl)-9, 10-dihydro-9-oxa-10-phosphaphenanthrene-10-oxide (DHQEP) as illustrated by the following chemical formula:

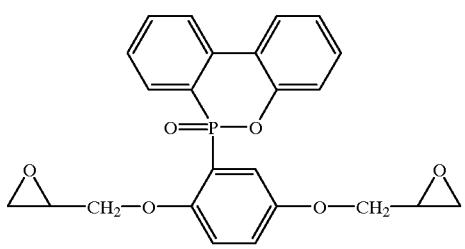

The synthesis of DHQEP as an effective flame retardant and thermal stabilizer for epoxy resins is described in Cho, Ching-sheng/Chen, Leo-wang/Chiu, Yie-shun; Polymer Bulletin 41, 45–52 (1998), In another preferred embodiment the epoxy resin material (I) used in the present invention may (C) a mixture of (1) an epoxy compound containing at least two epoxy groups, and (2) a phosphorus-containing compound. It is possible to add the phosphorus-containing compound (C) and the epoxy resin compound (C) to the overall composition of the present invention in order to form the epoxy resin material (I) in-situ.

In another preferred embodiment, the epoxy resin material (I) which is added to the overall composition of the present invention, may be (D) the reaction product of (1) an epoxy resin and (2) a phosphorus-containing DI compound capable of reacting with the epoxy resin.

The aforementioned epoxy resin (C1) or (D1) is preferably one which has no lower alkyl aliphatic substituents, for example the glycidyl ether of a phenol novolac, or the glycidyl ether of bisphenol-F.

The most preferred epoxy resins (C1) or (D1) are epoxy novolac resins (sometimes referred to as epoxidised novolac resins, a term which is intended to embrace both epoxy phenol novolac resins and epoxy cresol novolac resins). Such epoxy compounds have the following general chemical structural Formula VII:

Formula VII

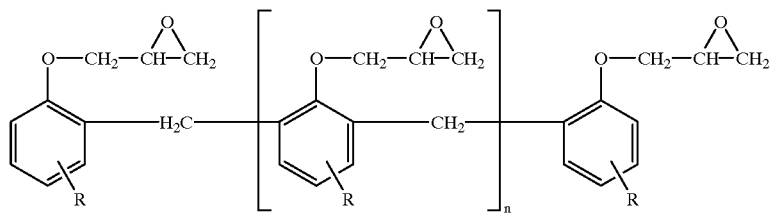

wherein "R" a is hydrogen or a $C_1$–$C_3$ alkyl, e.g., methyl and "n" is 0 or an integer from 1 to 10. "n" preferably has an average value of from 0 to 5.

Epoxy novolac resins (including epoxy cresol novolac resins) are readily commercially available, for example under the trade names D.E.N.™ (Trademark of The Dow Chemical Company), Quatrex™, Tactix™. The materials of commerce generally comprise mixtures of various species of the above formula and a convenient way of characterizing such mixtures is by reference to the average, n', of the values of n for the various species. Preferred epoxy novolac resins for use in accordance with the present invention are those in which n has a value of from about 2.05 to about 10, more preferably from about 2.5 to about 5.

The phosphorus-containing compound or monomer (C2) or (D2) contains some reactive groups such as a phenolic group, an acid group, an amino group, an acid anhydride group, or a phosphinate group (P—H) which can react with the epoxy groups of the epoxy resin compound (C1) or (D1).

In a most preferred embodiment of the present invention the phosphorus-containing monomer (C2) or (D2) used in the present invention is for example, 9,10-dihydro-9-oxa-10-phosphaphenanthrene-10-oxide such as "Sanko-HCA" commercially available from SANKO of Japan or "Struktol Polydis PD 3710" commercially available from Schill-Seilacher of Germany; 10-(2',5'-dihydroxyphenyl)-9,10-dihydro-9-oxa- 10-phosphaphenanthrene-10-oxide (HCA-HQ); bis(4-hydroxyphenyl)phosphine oxide; tris(2-hydroxyphenyl)phosphine oxide; dimethyl-1-bis(4-hydroxyphenyl)-1-phenyhnethylphonate, an isomeric mixture of tris(2-hydroxymethylphenyl)phosphine oxides; or tris(2-hydroxy-5-methylphenyl) phosphine oxide; and mixtures thereof.

The phosphorus-containing compound (C2) or (D2) of the present invention may contain on average one or more than one functionality capable of reacting with the epoxy groups. Such phosphorus-containing compound preferably contains on average 0.9 to 3 functional groups capable of reacting with epoxy resin.

The compositions of the present invention preferably contain a catalyst (III) capable of promoting the reaction of the cross-linker of the present invention, and/or the phosphorus-containing compounds with the epoxy resin and promoting the curing of the epoxy resin.

Examples of suitable catalyst materials useful in the present invention include for example compounds containing or amine, phosphine, ammonium, phosphonium, arsonium or sulfonium moieties. Particularly preferred catalysts are heterocyclic nitrogen-containing compounds.

The catalysts (III) (as distinguished from cross-linkers) preferably contain on average no more than about 1 active hydrogen moiety per molecule. Active hydrogen moieties include hydrogen atoms bonded to an amine group, a phenolic hydroxyl group, or a carboxylic acid group. For instance, the amine and phosphine moieties in catalysts are preferably tertiary amine or phosphine moieties; and the ammonium and phosphonium moieties are preferably quaternary ammonium and phosphonium moieties. Among preferred tertiary amines that may be used as catalysts are those mono- or polyamines having an open-chain or cyclic structure which have all of the amine hydrogen replaced by suitable substituents, such as hydrocarbyl radicals, and preferably aliphatic, cycloaliphatic or aromatic radicals. Examples of these amines include, among others, 1,8-diazabicyclo (5.4.0)undec-7-en (DBU), methyl diethanol amine, triethylamine, tributylamine, dimethyl benzylamine, triphenylamine, tricyclohexyl amine, pyridine and quinoline. Preferred amines are the trialkyl, tricycloalkyl and triaryl amines, such as triethylamine, triphenylamine, tri-(2, 3-dimethylcyclohexyl)amine, and the alkyl dialkanol amines, such as methyl diethanol amines and the trialkanolamines such as triethanolamine. Weak tertiary amines, for example, amines that in aqueous solutions give a pH less than 10 in aqueous solutions of 1 M concentration, are particularly preferred. Especially preferred tertiary amine catalysts are benzyldimethylamine and tris-(dimethylaminomethyl) phenol.

Examples of suitable heterocyclic nitrogen-containing catalysts (III) include those described in U.S. Pat. No. 4,925,901. Preferable heterocyclic secondary and tertiary amines or nitrogen-containing catalysts which can be employed herein include, for example, imidazoles, benzimidazoles, imidazolidines, imidazolines, oxazoles, pyrroles, thiazoles, pyridines, pyrazines, morpholines, pyridazines, pyrimidines, pyrrolidines, pyrazoles, quinoxalines, quinazolines, phthalozines, quinolines, purines, indazoles, indoles, indolazines, phenazines, phenarsazines, phenothiazines, pyrrolines, indolines, piperidines, piperazines and combinations thereof. Especially preferred are the alkyl-substituted imidazoles; 2,5-chloro-4-ethyl imidazole; and phenyl-substituted imidazoles, and mixtures thereof. Even more preferred are N-methylimidazole; 2-methylimidazole; 2-ethyl-4-methylimidazole; 1,2-dimethylinidazole; and 2-methylimidazole. Especially preferred is 2-phenylimidazole.

Preferably a Lewis acid (IV) is also employed in the composition of the present invention, especially when the catalyst (III) is, particularly a heterocyclic nitrogen-containing compound.

Examples of heterocyclic nitrogen-containing catalysts (III) which are preferably used in combination with Lewis acids (IV) are those described in EP-A-526488, EP A 0458502 & GB A 9421405.3. Examples of suitable Lewis acids useful in the present invention include halides, oxides, hydroxides and alkoxides of zinc, tin, titanium, cobalt, manganese, iron, silicon, aluminium, and boron, for example Lewis acids of boron, and anhydrides of Lewis acids of boron, for example boric acid, metaboric acid, optionally substituted boroxines (such as trimethoxyboroxine), optionally substituted oxides of boron, alkyl borates, boron halides, zinc halides (such as zinc chloride) and other Lewis acids that tend to have a relatively weak conjugate base. Preferably the Lewis acid is a Lewis acid of boron, or an anhydride of a Lewis acid of boron, for example boric acid, metaboric acid, an optionally substituted boroxine (such as trimethoxy boroxine, trimethyl boroxine or triethyl boroxine), an optionally substituted oxide of boron, or an alkyl borate. The most preferred Lewis acid is boric acid. These Lewis acids are very effective in curing epoxy resins when combined with the heterocyclic nitrogen-containing compounds, referred to above.

The Lewis acids and amines can be combined before mixing into the formulation or by mixing with the catalyst in-situ, to make a curing catalyst combination. The amount of the Lewis acid employed is preferably at least 0. 1 moles of Lewis acid per mole of heterocyclic nitrogen compound, more preferably at least 0.3 moles of Lewis acid per mole of heterocyclic nitrogen-containing compound.

The formulation preferably contains no more than 3 moles of Lewis acid per mole of catalyst and more preferably contains no more that 2 moles of Lewis acid per mole of catalyst. The total amount of the catalyst is from about 0.1 wt % to about 3 wt %, based on the total weight of the composition, preferably from about 0. 1 wt % to about 2%.

The compositions of the present invention may also optionally contain one or more additional flame retardant additives (V), including for example, red phosphorous or liquid or solid phosphorus-containing compounds, for example, ammonium polyphosphate, a phosphite, or phosphazenes, nitrogen-containing fire retardants and/or synergists, for example melamines, urea, cynamide, guanidine, cyanuric acid, isocyanuric acid and derivatives of those nitrogen-containing compounds, halogenated flame retardants, halogenated epoxy resins (especially brominated epoxy resins) synergistic phosphorus-halogen containing chemicals or compounds containing salts of organic acids, inorganic metal hydrates, boron or antimony. Examples of suitable additional flame retardant additives are given in a paper presented at "Flame retardants—101 Basic Dynamics—Past efforts create future opportunities", Fire Retardants Chemicals Association, Baltimore Marriot inner harbour hotel, Baltimore Md., Mar. 24–27 1996.

When additional fire retardants which contain a phosphorus element are present in the composition of the present invention, the phosphorus element-containing fire retardants are generally present in amounts such that the total phosphorous content of the epoxy resin composition is from about 0.2 wt % to about 5 wt %.

Other non-epoxy, phosphorus additives which can be used in the present invention may include for example phosphorus-guanamine having the following chemical structure:

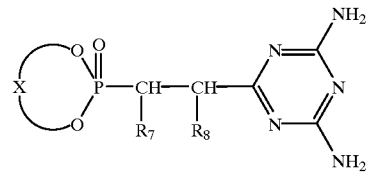

where X is $CR_3R_4$-$(CR_1R_2)n$-$CR_5R_6$ or o-phenylidene, n is 0 or 1 $R_1$–$R_8$ may be the same or different and represent H, $CH_3$, $C_2H_5$.

The phosphorus-quanamine above is found to be a highly suitable alternative to brominated epoxy resins for printed circuit board (PCB) applications as described in Buser, Antonius Johannes Wilhelmus/Schutyser, Jan Andre Jozef, Akzo Nobel N. V. European Pat. 0825217 Al (25.02.1998) and Buser, Antonius Johannes Wilhelmus/Schutyser, Jan Andre Jozef, Akzo Nobel N. V. European Pat. WO 98/07731 (26.02.98).

Another phosphorus additive useful in the present invention is "Antiblaze #1045" available from Albright and Wilson. Antiblaze #1045 is a cyclic phosphonate dimer containing 20.8% phosphorous and has the following structure:

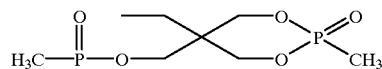

The following amino triazine phosphates are also phosphorus additives which may be used in the present invention:

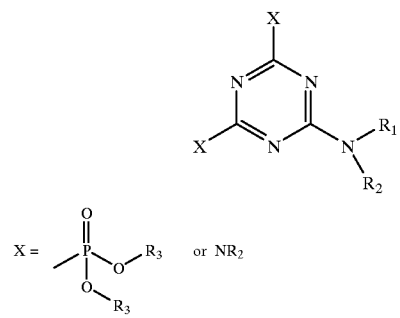

where $R_1$, $R_2$ and $R_3$ is independently H or a $C_1$–$C_{40}$ alkyl group such as methyl.

The composition of the present invention may also include other inorganic fillers (VI), for example fillers such as aluminum trihydroxide e.g. "Martinal OL-104" from Martinswerke GmbH; magnesium hydroxide, e.g. "Zerogen 30" available from Martinswerke GmbH; and ammonium polyphosphate, e.g. "Exolit 700" available from Clariant GmbH. The aforementioned inorganic fillers can be added to the composition of the present invention to improve the flame retardant properties of the composition.

Solvents (VIII) may also optionally be used in the composition of the present invention. When a solvent is used it may include for example, propylene glycolmethylether (Dowanol PM™), methoxypropylacetate (Dowanol PMA™), methylethylketone (MEK), acetone, methanol, and combinations thereof. When a solvent is used in the present invention, the amount of solvent present in the epoxy resin composition of the present invention is generally form 0 wt % to about 50 wt %; preferably from about 10 wt % to about 40 wt % and more preferably from about 10 wt % to about 35 wt %, depending on the end use application of the epoxy resin composition.

Optionally, in some applications it may be desirable to add a small amount of a halogenated epoxy resin (IX, provided the halogenated epoxy resin is added in an amount such that the halogen content of the overall epoxy resin composition of the present invention is less than 10 weight percent.

The compositions of the present invention can be produced by mixing all the components together in any order. Preferably, the compositions of the present invention can be produced by preparing a first composition comprising the epoxy resin, and the second composition comprising the crosslinking agent. Either the first or the second composition may also comprise a phosphorus-containing compound a curing catalysts a multi-functional phenolic co-crosslinking agent and/or a nitrogen-containing co-crosslinking agents. All other components may be present in the same composition, or some may be present in the first, and some in the second. The first composition is then mixed with the second composition, and cured to produce a fire retardant epoxy resin.

The compositions of the present invention can be used to make composite materials by techniques well known in the industry much as by pultrusion, moulding, encapsulation, or coating.

The present invention is particularly useful for making B-staged prepregs and laminates by well known techniques in the industry.

A number of preferred embodiments of the present invention are illustrated, in the following specific Examples.

EXAMPLE 1

Synthesis of the Crosslinker of Formula II

A solution of tritolylphosphate (a mixture of meta (70%) and para (30%) isomers) (147 g, 0.40 mol) in dry tetrahydrofuran (THF) (100 mL) was added dropwise to a solution of 1.5 M lithium diisopropyl amide (LDA) (1200 mL, 1.8 mol) in dry THF (400 mL) at about −78° C. in a dry ice isopropanol bath. On completion of the above addition, the solution was stirred at about −78° C. for two hours. Then, the dry ice bath was removed and the reaction mixture was allowed to warm to 20° C.–25° C. over three hours. Isopropanol (150 mL) was added to the mixture to react with any excess LDA present in the mixture. The resultant solution was then poured into an HCl solution (1850 mL of 2.3 M, 4.2 mol). A milky yellow precipitate was initially obtained, which dissolved on stirring to yield a two phase system consisting of an organic layer and an aqueous layer. The organic layer was separated from the two phase system and then methylene chloride (500 mL) was added to the organic layer. The resulting organic layer solution was washed with 5% HCl (2×500 mL) and water (2×500 mL). The solvent in the solution was removed under reduced pressure (80° C., 20 mm Hg, 2 hours and 150° C., 1–3 mm Hg, 2 hours) to yield an amber solid, which was identified as the chemical structure of Formula II by $^1$H NMR spectroscopy. The yield was 139 g, (94%).

EXAMPLES 2–4

Laminate Preparation and Testing

Product from the above synthesis (known as Formula II) were used to prepare two solutions. Firstly, Formula II was dissolved into methyl ethyl ketone (MEK) to produce a solution at 457% solids content. Secondly, Formula II was dissolved into dimethyl foramide (DMF) to produce a solution at 50% solids content. The Formula II solutions where then mixed with two types of epoxy resins and quantities of boric acid solution and 2-methyl imidazole (2-MI) solution in the portions indicated below to produce varnishes shown as Examples 2, 3 and 4;

| Varnish Component | Example 2 Parts | Example 2 Weight used (g) | Example 3 Parts | Example 3 Weight used (g) | Example 4 Parts | Example 4 Weight used (g) |
| --- | --- | --- | --- | --- | --- | --- |
| D.E.N. ™ 438 (100% solids epoxy novolac resin) | 100 | 150 | 100 | 115 | — | — |
| XZ92403.00(1) (80% solids epoxy resin in MEK) | — | — | — | — | 100 | 250 |
| Formula II(45% solids in MEK) | 68 | 226.7 | — | — | — | — |
| Formula II(50% solids in DMF) | — | — | 68 | 156.4 | 41 | 164 |
| Boric Acid(20% in Methanol) | 0.7 | 5.25 | 0.7 | 4.03 | 0.4 | 4.0 |
| 2-MI(10% in Methanol) | 0.7 | 10.5 | 0.7 | 8.05 | 0.4 | 8.0 |
| Varnish properties | | | | | | |
| Solids content of varnish % | | 67.0 | | 71.2 | | 68.1 |
| Varnish gel time 170° C. (seconds) | | 221 | | 211 | | 211 |
| Laminate properties | | | | | | |
| Tg measured by D.S.C. in C. | | n.m.* | | 175 | | 157 |
| UL-94 classification | | n.m. | | V-0 | | V-1 |
| Blister test/% $H_2O$ pick-up | | n.m. | | 20 minutes/0.33 40 minutes/0.45 | | 20 minutes/0.21 40 minutes/0.30 |

*n.m. = not measured
(1)XZ92403.00 is produced by and available from The Dow Chemical Company.

Several plies of glass cloth (10 cm$^2$, 7628 style from Procher S.A., France) were then individually soaked into the varnishes Examples 3 and 4. The impregnated glass sheets were then held into a circuited air laboratory oven at a temperature of 170° C. for 3 minutes. Then, up to 8 of the prepreg plies based on the varnishes Examples 3 and 4 where then sacked and press together in a laboratory minipress for 2 hours at 175° C. to produce the consolidated laminates Examples 3 and 4. Once the pressed laminates had cooled they where tested for glass transition temperature (Tg) by D.S.C., flame retardancy rating (employing the UL-94 classification method) and for blistering during solder dip exposure resulting from a pre-conditioning moisture pick-up method (IPC test method TM-650 conditions were employed). The later is more commonly referred to as the high pressure cooker test.

The data measured on the laminates Examples 3 and 4 indicate that robust materials, suitable for fabrication into printed wiring boards, can be produced. These materials are comparable to NEMI grade FR-4 electrical laminate substrate, produced with convention brominated flame retardant compounds, e.g. tetrabromo bisphenol-A (TBBA).

The IPC test methods employed in the Examples herein are the electrical laminate industry standard (The Institute For Interconnection And Packaging Electronic Circuits, 3451 Church Street, Evanston, Ill. 60203), as follows:

| Method | IPC-Test Method Number: |
|---|---|
| Reactivity (varnish) | IPC-TM-650-5.1.410 |
| Rest Geltime @ 170° C., seconds | IPC-TM-650-2.3.18 |
| Mil Flow, weight percent (wt. %) | IPC-TM-650-2.3.17 |
| Tg, ° C. | IPC-TM-650-2.4.25 |
| Copper peel strength | IPC-TM-650-2.4.8 |
| NMP-pick-up | Dow method C-TS-AA-1012.00 |
| Pressure Cooker Test, wt. % water pick-up & % passed solder bath @ 260° C. | IPC-TM-650-2.6.16 |
| UL94 Flammability | IPC-TM-650-2.3.10 |

What is claimed is:

1. A crosslinking agent comprising an isomeric mixture of two or more triaryl phosphine oxide isomer compounds having the following general chemical structural formula:

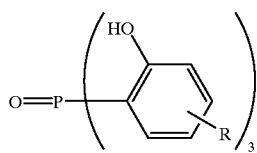

Formula I wherein each R, is independently the same or different, wherein each R on each phenyl ring of the above formula may be in the 3, 4, 5 or 6 position, and wherein each R is independently a hydrogen or a $C_1$–$C_{10}$ alkyl group, with the proviso that at least one R is a $C_1$–$C_{10}$ alkyl group; and wherein said isomeric mixture has a solubility of at least greater than 30% solids contents in an aprotic or protic solvent.

2. The crosslinking agent of claim 1 wherein R is a methyl group.

3. The crosslinking agent of claim 1 wherein at least one of the isomers in the isomeric mixture contains a 2-hydroxy-4-methylphenyl moiety.

4. The crosslinking agent of claim 1 wherein at least one of the isomers in the isomeric mixture contains a 2-hydroxy-5-methylphenyl moiety.

5. The crosslinking agent of claim 1 wherein the isomeric mixture contains at least a mixture of a 2-hydroxy-4-methylphenylmoiety and 2-hydroxy-5-methylphenylmoiety.

6. The crosslinking agent of claim 5 wherein the ratio of 2-hydroxy-4-methylphenyl moiety to 2-hydroxy-5-methylphenyl moiety is from about 99:1 to about 1:99.

7. A curable epoxy resin composition comprising:
(a) a curable epoxy resin; and
(b) as a curing agent, an effective curing amount of a phosphorus element-containing compound having the following general chemical structural Formula I:

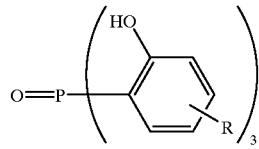

Formula I wherein each R, independently is the same or different, wherein each R on each phenyl ring of the above formula may be in the 3, 4, 5 or 6 position, and wherein each R is hydrogen or a $C_1$–$C_{10}$ alkyl group; and wherein said compound has a solubility of at least greater than 30% solids contents in an aprotic or protic solvent.

8. The composition of claim 7 wherein R is hydrogen.

9. The composition of claim 7 wherein R is a methyl group.

10. The composition of claim 9 wherein R is in the 5 position of the phenyl ring.

11. The composition of claim 7 wherein the curing agent is an isomeric mixture of two or more different triaryl phosphine oxide isomer compounds having the general chemical structural formula of Formula I.

12. The composition of claim 11 wherein the isomeric mixture contains a 2-hydroxy-4-methylphenyl moiety.

13. The composition of claim 11 wherein the isomeric mixture contains a 2-hydroxy-5-methylphenyl moiety.

14. The composition of claim 11 wherein the isomeric mixture contains at least a mixture of a 2-hydroxy-4-methylphenyl moiety and a 2-hydroxy-5-methylphenyl moiety.

15. The composition of claim 14 wherein the ratio of 2-hydroxy-4-methylphenyl moiety to 2-hydroxy-5-methylphenyl moiety is from about 99:1 to about 1:99.

16. The composition of claim 11 wherein the crosslinking agent is an isomeric mixture containing at least tris(2-hydroxy-5-methylphenyl)phosphine oxide.

17. A laminate prepared from the curable composition of claim 7.

18. A flame retardant phosphorus element-containing epoxy resin composition substantially free of halogen, comprising:
(I) a non-halogenated epoxy resin material selected from:
(A) an non-halogenated, non-phosphorus element-containing epoxy resin;
(B) a non-halogenated phosphorus element-containing epoxy resin;
(C) a mixture of:
(1) a non-halogenated, non-phosphorus element-containing epoxy resin, and
(2) a phosphorous element-containing compound;
(D) a reaction product of:
(1) a non-halogenated epoxy resin and
(2) a phosphorus element-containing compound; or
(E) a combination of two or more of components (A) to (D); and
(II) a phosphorus element-containing crosslinking agent having the following general chemical structural Formula I:

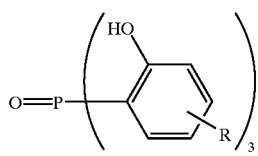

Formula I wherein R is independently hydrogen or a $C_1$–$C_{10}$ allyl group, in a sufficient amount to provide an epoxy resin network.

19. The composition of claim 18 wherein R is hydrogen.

20. The composition of claim 18 wherein R is a methyl group.

21. The composition of claim 18 wherein the phosphorus element-containing compound (2) includes a functionality selected from an epoxy, a phosphine, a hydroxy, an anhydride, or an acid functionality.

22. The composition of claim 21 wherein the phosphorous element-containing compound (2) is present in an amount sufficient to provide from about 0.2 weight percent to about 3.5 weight percent phosphorous in the curing composition.

23. The composition of claim 18 including:
(III) a catalyst capable of promoting the reaction of the crosslinking agent with the epoxy resin material.

24. The composition of claim 23 wherein the catalyst is present in an amount of from about 0.1 to about 3 weight percent.

25. The composition of claim 23 including: (IV) a Lewis acid.

26. The composition of claim 25 wherein the Lewis acid is present in an amount of up to about 2 moles per mole of catalyst.

27. The composition of claim 18 including: (V) a flame retardant additive.

28. The composition of claim 27 wherein the flame retardant additive is selected from red phosphorous or liquid or solid phosphorus element-containing compounds.

29. The composition of claim 27 wherein the additive is ammonium polyphosphate, a phosphite, or phosphazenes, nitrogen-containing fire retardants and/or synergists.

30. The composition of claim 27 wherein the flame retardant additive is melamines, urea, cynamide, guanidine, cyanuric acid, isocyanuric acid or derivatives of those nitrogen-containing compounds, halogenated flame retardants, halogenated epoxy resins, synergistic phosphorus-halogen containing chemicals or compounds containing salts of organic acids, inorganic metal hydrates, boron or antimony or mixtures thereof.

31. The composition of claim 28 wherein the phosphorus element-containing flame retardants is present in an amount such that the total phosphorus content of the epoxy resin composition is from about 0.2 wt % to about 5 wt %.

32. The composition of claim 27 wherein the flame retardant additive is a halogenated bisphenol A in an amount less than 10 weight percent.

33. The composition of claim 18 including: (VI) a filler material.

34. The composition of claim 33 wherein the filler is an inorganic filler material.

35. The composition of claim 33 wherein the filler is a flame retardant filler material.

36. The composition of claim 18 including: (VII) a co-crosslinking agent different from the phosphorus element-containing crosslinking agent (II).

37. The composition of claim 36 wherein the co-crosslinking agent (VII) is a phenolic crosslinking agent.

38. The composition of claim 36 wherein the co-crosslinking agent (VII) is a nitrogen-containing co-crosslinking agent.

39. The composition of claim 38 wherein the nitrogen-containing crosslinking agent is a nitrogen-containing crosslinking agent having an amine functionality of at least 2.

40. The composition of claim 39 wherein the co-crosslinking agent is present in an amount of from 0 to about 40% of the stoichiometric amount needed to cure the epoxy resin.

41. The composition of claim 18 wherein the phosphorus element-containing epoxy resin (B) is obtained by epoxidizing a phosphorus element-containing compound.

42. The composition of claim 18 wherein the phosphorus element-containing epoxy resin (B) is obtained by reacting an epoxy resin with a phosphorus element-containing compound capable of reacting with the epoxy resin.

43. The composition of claim 18 including (VIII) a halogenated epoxy resin compound in an amount such that the halogen content in the epoxy resin composition is less than 10 weight percent.

44. The composition of claim 43 wherein the non-halogenated, non-phosphorus element-containing epoxy resin (A) is diglycidyl ether of bisphenol A.

45. The composition of claim 18 wherein the phosphorus element-containing crosslinking agent is an isomeric mixture of two or more different triaryl phosphine oxide isomer compounds having the general chemical structural formula of Formula I.

46. The composition of claim 45 wherein the isomeric mixture contains a 2-hydroxy-4-methylphenyl moiety.

47. The composition of claim 45 wherein the isomeric mixture contains a 2-hydroxy-5-methylphenyl moiety.

48. The composition of claim 45 wherein the isomeric mixture contains at least a mixture of a 2-hydroxy-4-methylphenyl moiety and a 2-hydroxy-5-methylphenyl moiety.

49. The compositions of claim 18 wherein the non-halogenated phosphorus element-containing epoxy resin (B) is an isomeric mixture of two or more different triaryl phosphine oxide isomer compounds having the general chemical structural formula of Formula V:

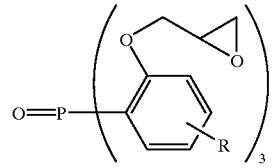

wherein R is independently a hydrogen or a $C_1$–$C_{10}$ alkyl group.

50. The composition of claim 49 wherein with the isomeric mixture contains a 2-glycidyloxy-4-methylphenyl moiety.

51. The composition of claim 49 wherein the isomeric mixture contains 2-glycidyloxy-5-methylphenyl moiety.

52. The composition of claim 49 wherein the isomeric misture contains at least a mixture of a 2-glycidyloxy 4-methylphenyl moiety and a 2-glycyloxy-5-methylphenyl moiety.

53. A "B-stage" material made from the composition of claim 18.

54. A laminate made from the composition of claim 18.

55. A process for making a curable epoxy resin composition comprising mixing:

(a) a curable epoxy resin; and
(b) as a curing agent, an effective curing amount of a phosphorus element-containing compound having the following general chemical structural Formula I:

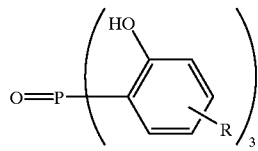

Formula I wherein each R, is independently the same or different, wherein each R on each phenyl ring of the above formula may be in the 3, 4, 5 or 6 position, and wherein each R is independently a hydrogen or a $C_1$–$C_{10}$ alkyl group; and wherein said compound has a solubility of at least greater than 30% solids content in an aprotic or protic solvent.

56. A process for making a flame retardant phosphorus element-containing epoxy resin substantially free of halogen comprising mixing:

(I) a non-halogenated epoxy resin material selected from:
(A) an non-halogenated, non-phosphorus element-containing epoxy resin;
(B) a non-halogenated phosphorus element-containing epoxy resin;
(C) a mixture of:
(1) a non-halogenated, non-phosphorus element-containing epoxy resin, and
(2) a phosphorous element-containing compound;
(D) a reaction product of:
(1) a non-halogenated epoxy resin and
(2) a phosphorus element-containing compound: or
(E) a combination of two or more of components (A) to (D); and (II) a phosphorus element-containing crosslinking agent having the following general chemical structural Formula I:

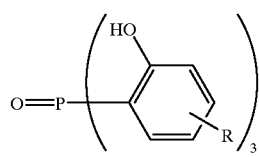

Formula I wherein R is hydrogen or a $C_1$–$C_{10}$ allyl group, in a sufficient amount to provide an epoxy resin network.

* * * * *